United States Patent
Nadol, Jr.

[11] Patent Number: 5,480,433
[45] Date of Patent: Jan. 2, 1996

[54] METHOD OF TREATING HEARING LOSS

[76] Inventor: Joseph B. Nadol, Jr., 640 Charles River Rd., Needham, Mass. 02192

[21] Appl. No.: 247,106

[22] Filed: May 20, 1994

Related U.S. Application Data

[62] Division of Ser. No. 139,557, Oct. 20, 1993, Pat. No. 5,356,430, which is a continuation of Ser. No. 712,430, Jun. 10, 1991, abandoned.

[51] Int. Cl.$^6$ ................... A61F 2/18; A61F 2/04
[52] U.S. Cl. .................................. 623/10; 623/12
[58] Field of Search ................... 623/10, 11, 12; 604/96–103, 49, 892.1; 600/37; 128/898

[56] References Cited

U.S. PATENT DOCUMENTS

| | | |
|---|---|---|
| Re. 33,561 | 3/1991 | Levy ........................... 604/96 X |
| 1,045,917 | 12/1912 | Valiquet . |
| 3,473,170 | 10/1969 | Haase et al. . |
| 3,875,595 | 4/1975 | Froning . |
| 3,916,873 | 11/1975 | Wasserman . |
| 4,077,069 | 3/1978 | Perkins . |
| 4,094,303 | 6/1978 | Johnston . |
| 4,175,563 | 11/1979 | Arenberg et al. . |
| 4,297,748 | 11/1981 | Moloy ........................... 623/10 |
| 4,300,557 | 11/1981 | Refojo et al. . |
| 4,416,267 | 11/1983 | Garren et al. ........................... 604/96 X |
| 4,419,095 | 12/1983 | Nebergall et al. ........................... 604/96 |
| 4,490,421 | 12/1984 | Levy ........................... 604/96 X |
| 4,497,074 | 2/1985 | Rey et al. ........................... 623/12 |
| 4,553,959 | 11/1985 | Hickey et al. ........................... 604/96 |
| 4,575,371 | 3/1986 | Nordqvist et al. ........................... 604/96 |
| 4,597,764 | 7/1986 | Black ........................... 623/10 |
| 4,685,447 | 8/1987 | Iversen et al. . |
| 4,695,275 | 9/1987 | Bruce et al. . |
| 4,739,758 | 4/1988 | Lai et al. . |
| 4,888,017 | 12/1989 | DeVore et al. ........................... 623/10 |
| 4,899,747 | 2/1990 | Garren et al. ........................... 604/96 X |
| 4,950,239 | 8/1990 | Gahara et al. ........................... 604/96 |
| 4,976,690 | 12/1990 | Solar et al. ........................... 604/96 |
| 5,036,868 | 8/1991 | Berggren et al. ........................... 604/96 X |
| 5,084,061 | 1/1992 | Gau et al. ........................... 604/96 X |
| 5,092,839 | 3/1992 | Kipperman ........................... 604/96 X |

FOREIGN PATENT DOCUMENTS

| | | |
|---|---|---|
| 0103481 | 9/1983 | European Pat. Off. . |
| 0174141 | 8/1985 | European Pat. Off. . |
| 1357725 | 2/1963 | France . |
| 2383673 | 3/1977 | France . |
| 1634-272-A | 3/1991 | U.S.S.R. . |

OTHER PUBLICATIONS

Gates, "Sulfur Hexafluoride Therapy," Arch Otolaryngol Commentary, Vo. 109, p. 357 (1983).

Andreasson et al., "Treatment With Sulfur Hexafluoride in Children With Serous Otitis Media," Arch Otolaryngol, vol. 109, pp. 358–359 S(1983).

Primary Examiner—Mary Beth O. Jones
Attorney, Agent, or Firm—Lahive & Cockfield

[57] ABSTRACT

For treatment of conductive hearing loss due, for example, to serous otitis media, a synthetic bubble is implanted in the hypotympanic cavity to displace fluid allowing free motion of the round window. A thin membrane provides the required degree of compliance, and is substantially impermeable to gases and water vapor, resulting in an extended lifetime. A large molecule inert filler gas may be used, either alone, or with normal gases to provide certain partial inflation states wherein osmotic ingress of smaller molecular gases causes sustained self-inflation of the bubble for a substantial time.

3 Claims, 4 Drawing Sheets

METHOD OF TREATING HEARING LOSS

This application is a divisional of application Ser. No. 08/139,557 filed on Oct. 20, 1993, now U.S. Pat. No. 5,356,430, which in turn is a continuation of application Ser. No. 07/712,430, filed on Jun. 10, 1991, now abandoned.

TECHNICAL FIELD

The present invention relates to hearing prostheses, and in particular to a synthetic bubble or balloon for implantation in the ear.

It has previously been proposed that certain forms of hearing loss or injury be remedied by artificial structures in the ear. Thus, for example, there have been proposals to replace a damaged eardrum by a drum formed of synthetic material. There has also been proposed, in U.S. Pat. No. 4,297,748, a method of placing an air or gas-filled pillow in the middle ear to block displacement of a tympanic membrane e.g., artificial eardrum, toward the round window. That pillow is made of elastic or other plastic material, and prevents the surgically reconstructed tympanic membrane from coming into proximity with or adhering to the round window following surgery. Other prosthetic devices have been proposed, including tympanic valves and funnel-like combinations of an ear horn with a membrane structure.

Such structures have tended to address mechanical defects in the structure of the ear, for example, by replacing or aligning damaged natural elements.

SUMMARY OF THE INVENTION

It is an object of the invention to provide prolonged relief from the conductive hearing loss caused by otitis media and related ailments of the middle ear.

It is another object of the invention to provide an acoustic coupling or impedance match between the outer and inner ear.

It is another object of the invention to provide an effective surgical method for restoration of hearing loss.

These and other desirable ends are to be attained in accordance with the present invention by implantation of a stable synthetic bubble structure into a position between the eardrum and the round window in the hypotympanic compartment of the middle ear. The bubble is a gas filled balloon, of bean-like or ovaloid shape, having cross dimensions of approximately two by three by five millimeters. Preferably, it has a tab extending therefrom for safely gripping and manipulating the bubble in position. In a preferred embodiment, the bubble is formed of a thin pliant material effective to achieve a good impedance match to the tympanum and to the round window, and is shaped or cast on a mandrel to impart a shape memory that maintains it in a suitable shape even when partially deflated.

At least the outer surface of the bubble is formed of biocompatible, and preferably hydrophobic material, and the bubble as a whole is substantially impermeable to water vapor. This construction, which may be achieved by a multilayer structure with different layers each selected to provide or enhance one or more of these characteristics, impedes the loss of inflation gas from the bubble.

In one preferred construction, the bubble is initially filled with a substantial portion, e.g. ten to fifty percent or more, of an unnatural, i.e., non-atmospheric, gas, preferably one to which the bubble wall is substantially impermeable. Nitrogen and oxygen are also present, but at lower partial pressures then in the surrounding atmosphere. The bubble then self-inflates by osmotic exchange with its environment, so that it remains filled for an extended period.

BRIEF DESCRIPTION OF DRAWINGS

These and other features of the invention will be understood from the description herein, including the drawings, wherein.

DETAILED DESCRIPTION OF INVENTION

Figure 1:
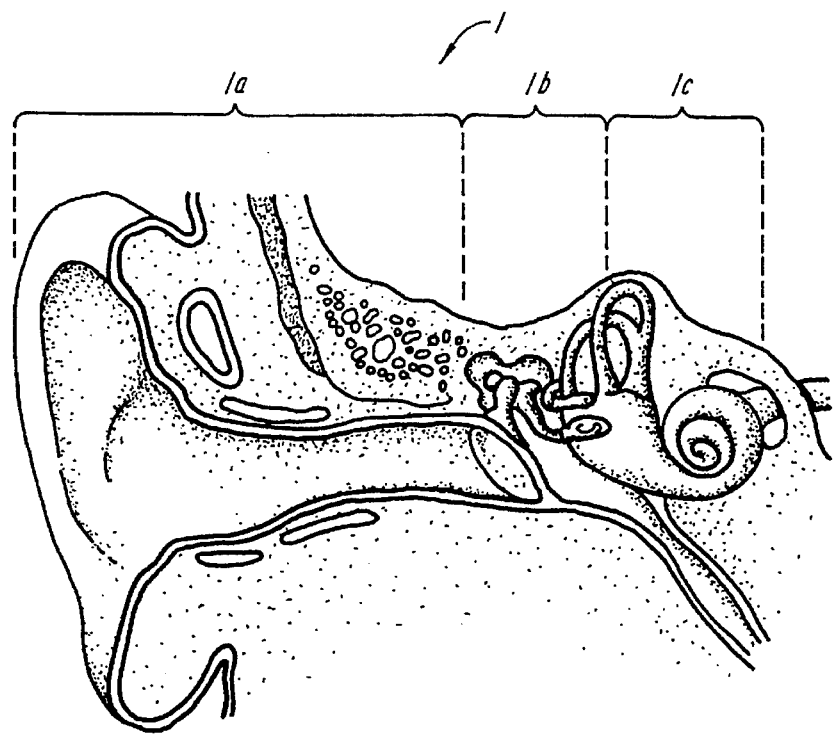
FIG. 1 shows a typical structure of the human ear.
Figure 2:
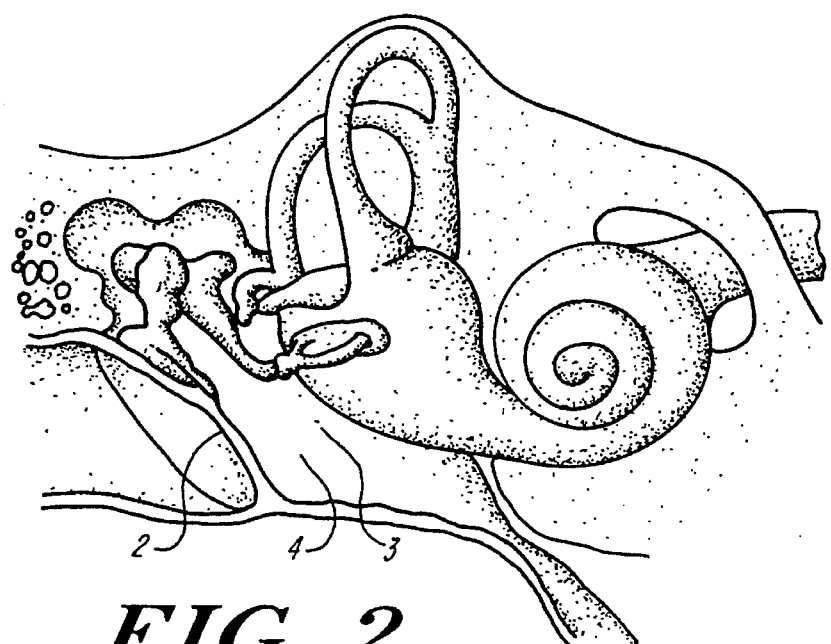
FIG. 2 shows a further typical structure of the human ear.

FIGS. 1 and 2 illustrate the human ear 1 and its operative structures by which the auricle, ear canal and drum of the outer ear 1a channel sound through the middle ear 1b to sensing structures of the inner ear 1c. The middle ear structures and their relative sizes and positions are shown in enlarged detail in FIG. 2, which advantageously shows the tympanic membrane 2, the round window 3 and the shape of the hypotympanic compartment 4 located between the opposed membranes.

While nominally filled with air maintained at atmospheric pressure via the eustachian tubes, this middle ear chamber can become chronically filled with fluid. Filling may occur because of blockage of the eustachian tube leading to pressure imbalances that cause fluid to exude from the surrounding tissue, or it may occur as a post-operative tissue inflammation, or because of infection or inflammatory processes which have a similar effect.

In cases in which the eustachian tube malfunctions, the normal air-filled middle ear becomes pathologically altered, resulting in retraction of the eardrum, an inflammatory response in the middle ear, or fluid in the middle ear space. These conditions can all lead to a conductive hearing loss due to the pathologically induced inefficiency of the middle ear sound transmitting system. This is a common finding in chronic active and in chronic inactive otitis media.

Figure 3:
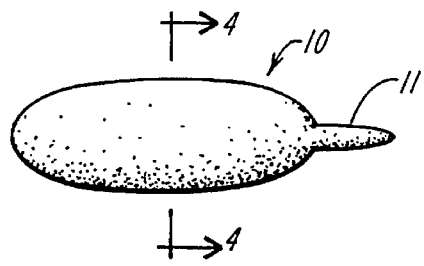
FIG. 3 illustrates one embodiment of a prosthetic device in accordance with the present invention.

Applicant's invention is a method and structure for ameliorating such hearing loss by providing a synthetic bubble 10 adapted for positioning between the eardrum and round window to displace fluid therebetween. By maintaining a reservoir of gas in a compressible form located proximate to the round window, the round window is assured a degree of compliance comparable to that of a normal ear. As shown in FIG. 3, the bubble 10 is a balloon structure having the shape of a jelly bean or gelatin capsule, the operative form of which is generally convex and ovaloid membrane enclosing a volume approximately two millimeters high by three millimeters wide by five millimeters long. These dimensions are selected to assure that the balloon will fit in the normal hypotympanic space. At one end, a tab 11 extends from the gas-filled body to provide a handle for surgical manipulation of the bubble in an ear without damaging the bubble wall. Preferably the tab contains a filler material or foil which renders it radioopaque for radiographic visualization.

For selection of material to manufacture a small balloon to fit within the middle ear and provide a compressible gas pocket, four primary criteria are believed to be desirable. The balloons must be able to flex with both pressure changes and sound vibrations, must be of low permeability to gases, must be stable and non-toxic to the biological environment of the middle ear, and must be easily formed into the desired balloon shape.

The effect that pressure variations which occur in a normal middle ear will have on a balloon's shape can be roughly quantified. During commercial airplane travel, the cabin pressure drops to roughly −15.5 cmHg (to 60.8 cmHg absolute). This corresponds to the atmospheric pressure at an altitude of 6000 feet, which covers the maximum altitude of American cites. This reduction in pressure creates a maximum increase in balloon volume of 25%, which corresponds to an increase in diameter of less than 8%. Such increase presents a very small strain for a common medical elastomer, such as a urethane. A balloon made from 0.003 inch thick or thicker urethane can readily withstand such pressure changes of the ear without harmful expansion into the delicate structures of the middle ear.

The useful life of the balloon will depend upon how long it takes for the gases to permeate out from its interior and for the balloon to collapse. The criteria for material selection of flexibility with low-permeability are competitive in that a thin, soft material is probably best to achieve good acoustic transmission but may have little ability to retard gas permeation. Therefore, the preferred construction is a multilayer balloon having at least two layers, preferably one including a soft polyurethane with a thin barrier material layer.

Some representative values of gas permeabilities are shown in Table 1. The barrier materials shown exhibit permeabilities up to 100 times lower than the urethane. Butyl rubber has been used in composites with urethanes in experimental medical membrane devices. Its permeability to water vapor is comparable to the other barrier materials but it is much more flexible. Its strength is very low and it is not very biocompatible, so to achieve an implantable balloon structure of this invention the butyl is sandwiched between layers of urethane to form a flexible, strong membrane of low permeability.

butyl rubber as an internal layer which serves as a barrier to entry of water vapor.

In selecting the urethane and butyl material, another material selection criterion is ease of fabrication. The urethanes mentioned above can be solvent cast onto mandrels in many shapes, and their thickness closely controlled. If desired, they may also be extruded. Butyl rubber is also easily solvent cast, and spraying techniques can also be used for fabrication of very thin and uniform sheets or layers.

The amount of flexibility which is necessary for good compressive response of a membrane and the balloon interior is unknown, and is difficult to quantify. When compared to air, the presence of any material in the middle ear will almost certainly reduce the level of sound perception by the inner ear. However, in comparison to the fluid found in a congested middle ear, a flexible compressible object with a thin balloon membrane should improve hearing. Therefore, the optimal amount of stiffness allowed in the balloon membrane must ultimately be determined by clinical observation.

With all of these considerations in mind, two urethanes were chosen for prototype consideration in constructing this invention, namely, those marketed under the trade designations Tecoflex 85A and/or Biomer, to be formed with a central layer of butyl rubber as a vapor barrier. Both of these urethanes are very flexible, and in conjunction with a layer of butyl permit the formation of flexible balloons of low permeability to water vapor and to normal atmospheric gases.

Figure 4:
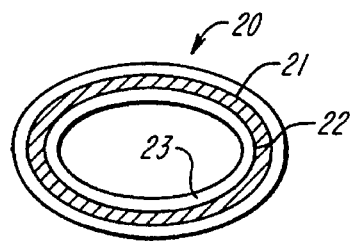
FIG. 4 is a cross-sectional view of the balloon shown in FIG. 3 illustrating the multilayer structure.

FIG. 4 illustrates the multilayer structure of one prototype balloon 20. An outer layer 21 of Tecoflex 85A urethane marketed under the trade designation 0.002–0.003 inches thick surrounds a 0.003 inch thick layer 22 of butyl rubber, which in turn is lined by an inner layer 23 of the same material as layer 21.

Bearing in mind the expected gas composition of atmospheric air and venous blood gases set out in Table 2, a number of permeation tests were performed on the trilaminate material of the balloon of FIG. 4 and on other monolayer and trilaminate materials in order to establish permeability values for modeling the osmotic evolution of gas in the balloon interior. Table 3 sets out the test results. One

TABLE 1

Permeability of Plastic Materials

| Material | Ultimate Strength (psi) | Elongation (%) | Water | Permeability (cc(STP)-cm/cm²-sec-cmHg) | | |
|---|---|---|---|---|---|---|
| | | | | $CO_2$ | $N_2$ | $O_2$ |
| Polyurethanes[1] | 100–10,000 | 100–1,000 | $8-16(10^{-6})$ | $2.5-10(10^{-10})$ | $0.25-.7(10^{-10})$ | $0.45-2(10^{-10})$ |
| HDPE[1] | 3,000–5,000 | 10–500 | $0.06(10^{-6})$ | $3.50(10^{-10})$ | $0.25(10^{-10})$ | $1.10(10^{-10}$ |
| PVDF[1] | 6,000 | 300 | $0.55(10^{-6})$ | $0.033(10^{-10})$ | $0.054(10^{-10})$ | $0.084(10^{-10})$ |
| Butyl Rubber[2] | 1,500 | 1,000 | $0.16(10^{-6})$ | NA | NA | NA |
| Acrylonitrile[1] | 9,000 | 3 | $0.94(10^{-6})$ | $0.01(10^{-10})$ | $0.0012(10^{-10})$ | $0.0039(10^{-10})$ |

HDPE = High Density Polyethylene
PVDF = Polyvinilidene Fluoride
[1]"Modern Plastics Encyclopedia", McGraw-Hill.
[2]"Development of an Implantable Integrated Electrically Powered Left Heart Assist System", Report to NHLBI, Thermo Electron, 1982.

Since the balloon must be in contact with the middle ear muscosal lining, a compatible material is required for the external surface. Suitable materials are the urethane marketed under the trade designation Tecoflex, or the polymer marketed under the trade designation Biomer marketed for medical use. One suitable balloon construction employs large-molecule biocompatible gas, sulfur hexafluoride ($SF_6$) was also evaluated in the tests as a possible long-lived filler material. All permeation values were normalized to the thickness of the sample layer.

TABLE 2

Typical Values of Gas Partial Pressures

| Gas | Partial Pressure (cmHg) |
|---|---|
| Atmospheric Air | |
| $CO_2$ | 0.02 |
| $H_2O$ Vapor | 4.70 |
| $O_2$ | 14.90 |
| $N_2$ | 56.40 |
| Total | 76.02 |
| Venous Blood Gases | |
| $O_2$ | 4.0 |
| $CO_2$ | 4.6 |

TABLE 3

Polymer Permeation Test Results

| | |
|---|---|
| Sulfur Hexafluoride ($SF_6$) | |
| 85A | $.056(10^{-10})$ |
| Biomer-butyl-Biomer | $.055(10^{-10})$ |
| Biomer-butyl-Biomer (Thick) | $.024(10^{-10})$ |
| 85A-butyl-85A | $.018(10^{-10})$ |
| Carbon Dioxide ($CO_2$) | |
| 85A | $1.66(10^{-10})$ |
| Biomer-butyl-Biomer | $1.41(10^{-10})$ |
| Biomer-butyl-Biomer (Thick) | $1.10(10^{-10})$ |
| Water Vapor ($H_2O$) | |
| 85A | $7.07(10^{-10})$ |
| Biomer-butyl-Biomer | $3.87(10^{-10})$ |
| Oxygen ($O_2$) | |
| 85A | $.497(10^{-10})$ |
| Biomer-butyl-Biomer | $.257(10^{-10})$ |
| Nitrogen ($N_2$) | |
| Biomer-butyl-Biomer | $.048(10^{-10})$ |
| Biomer is a trade designation for a polymer | |

Units = cc (STP)-cm/$cm^2$-sec-cmHg

Figure 5A:
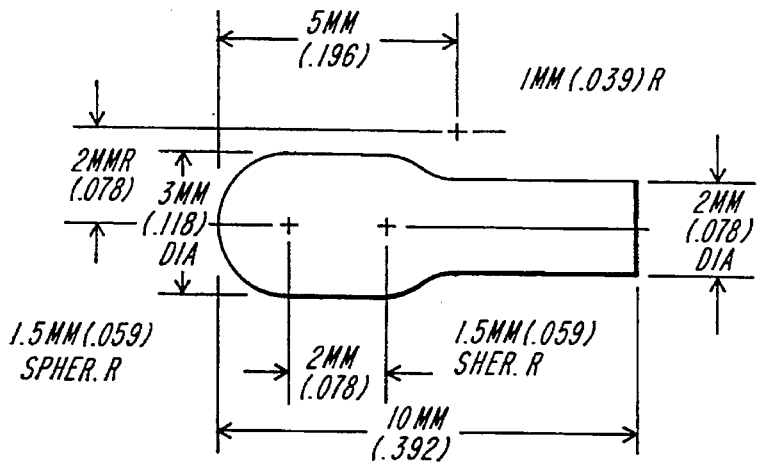
FIG. 5 is a view of a mandrel for forming the balloon of FIGS. 3 and 4.
Figure 5B:
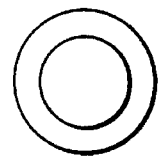

To manufacture prototype balloons, a trilaminate bubble structure was solvent cast by dipping a polished steel mandrel in solutions of the urethane and the butyl rubber polymers. FIG. 5 is an engineering drawing of the mandrel, showing dimensions and curvatures. To form an implantable balloon structure, the mandrel was repeatedly dipped in a solution of the balloon material (butyl or urethane) to form a shell of appropriate thickness. Following casting, the laminated balloon was peeled from the mandrel, filled, and sealed at its open end to form the tab 11 of FIG. 3.

A computer model was developed to simulate the composition and pressure of gas inside the balloon based on different initial inflation conditions. One simulation assumed that the balloon was initially full of atmospheric air to which was added a one cm Hg partial pressure of $SF_6$. Another simulation assumed the balloon was entirely filled with $SF_6$. In each case, on the assumption that the balloon maintained a constant volume, an iterative calculation was made to determine the amount of each gas entering or leaving the balloon based on differences in partial pressure of the gas on each side of the membrane.

The model predicted that the first set of inflation conditions would evolve by slowly losing $SF_6$, but otherwise maintaining the atmospheric gas components at a steady level. This would result in the occurrence of partial deflation over a period longer than one year. For the second simulation, an initial condition of pure $SF_6$ inflation, the model predicted the in-migration of all atmospheric gas components at a rate greatly exceeding the rate of $SF_6$ loss, so that over the course of months the balloon would spontaneously inflate.

Figure 6:
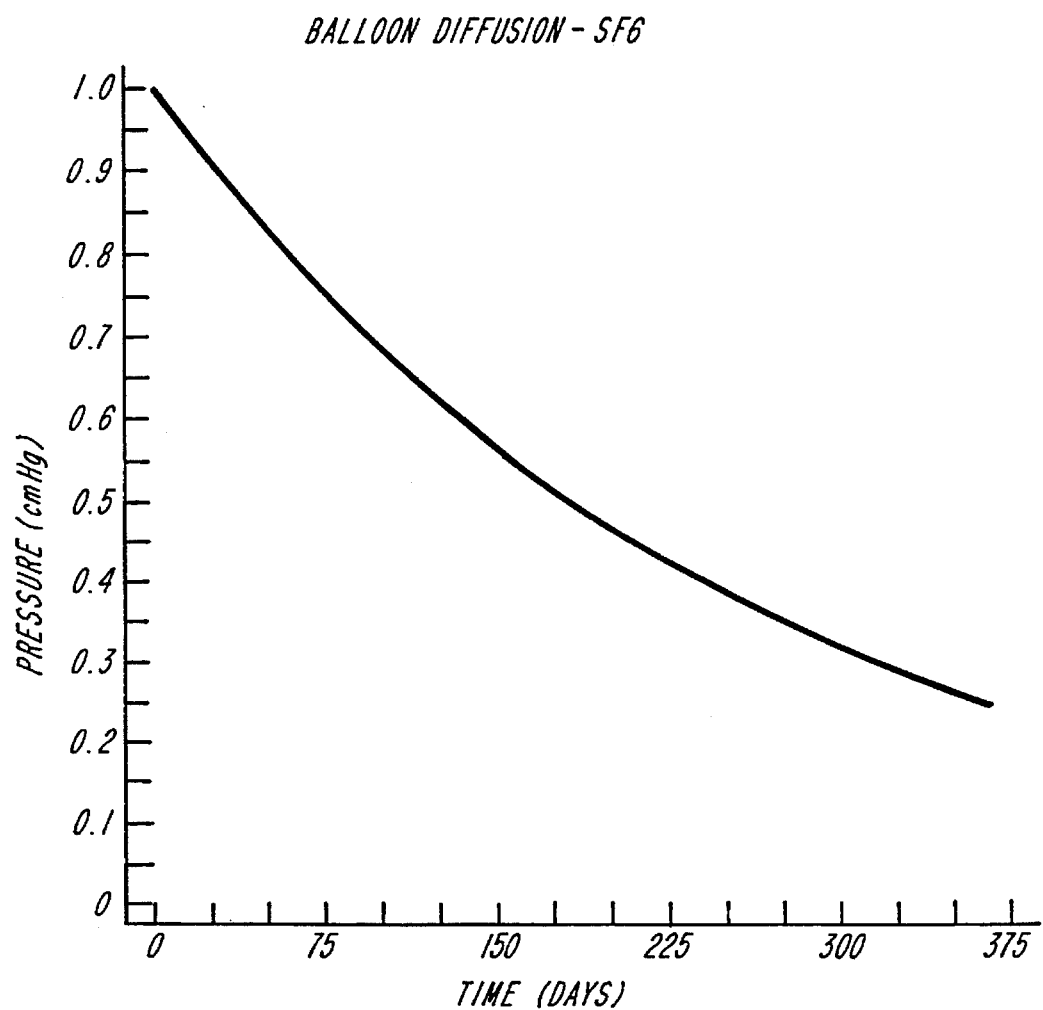
FIG. 6 is a graph of expected inflation characteristics of a trilaminate balloon like that of FIGS. 3 and 4.

FIG. 6 is a graph of the expected partial pressure of $SF_6$ remaining in a bubble over time, computed for a trilaminate bubble of Tecoflex 85A/butyl rubber/Tecoflex 85A having a wall thickness of eight mils; Tecoflex 85A being a trade designation for a urethane. Approximately 25% of the $SF_6$ remains after one year, and the rate of deflation tapers off gradually. Thus, if the bubble were partially inflated with normal blood gases at equilibrium partial pressures, a portion of $SF_6$ inflation could be initially employed in the fill mixture to provide a relatively stable, slowly diminishing pressure characteristic.

Figure 7:
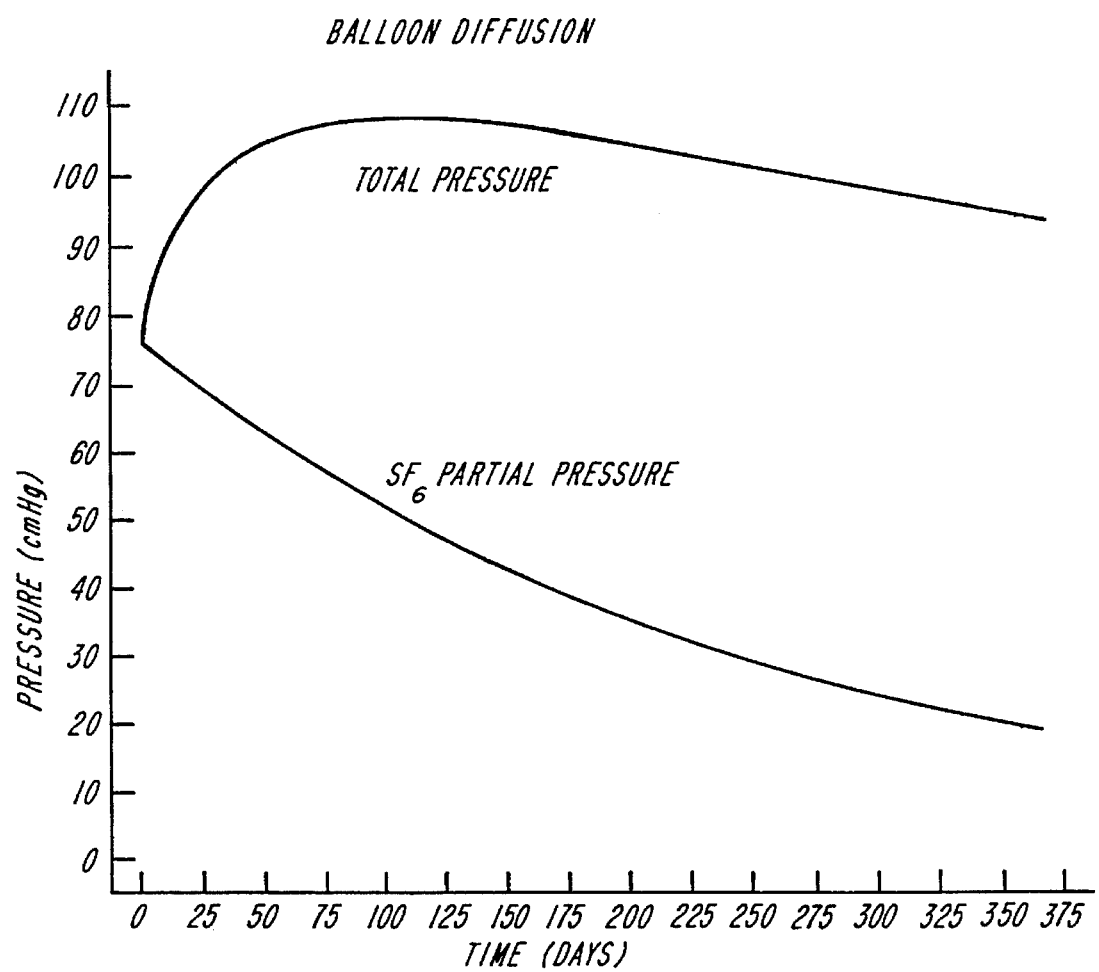
FIG. 7 is a graph of simulated inflation characteristics of a trilaminate balloon like that of FIGS. 3 and 4.

FIG. 7 is a graph of the simulation for a bubble initially inflated to atmospheric pressure with pure sulfur hexafluoride. Curve A represents the partial pressure of $SF_6$ as a function of time. Curve B shows the total pressure, including the gas components diffusing into the balloon interior. The model shows self-inflation to a fifty percent excess pressure over the course of several months, and greater than atmospheric pressure for a period of excess of one year.

The inflation characteristics, bursting pressure, and the like for the small bubble membrane are not readily predicted, and may not be susceptible to sufficient uniformity in manufacturing to allow empirical calibration, so it would be prudent to avoid such large excess pressure conditions. However, lesser levels of self-inflation may be accomplished by using several normal gases as a substantial fraction of the initial fill mixture, e.g., fifty to eighty percent, but at partial pressures that are lower than their partial pressures in the surrounding environment. Thus, the invention contemplates embodiments wherein one or more atmospheric gases together with an inert gas initially fill the synthetic bubble in proportions, and at partial pressures, such that the influx of atmospheric gases compensates for loss of inert gas to maintain the bubble inflated over time.

Short term in vitro testing of the sample balloons in an aqueous environment confirmed the self-inflation effect of the $SF_6$-filled balloons, and their ability to maintain an inflated state for periods in excess of several months. Furthermore, as anticipated, the shape-memory of solvent-cast balloons imparted to the balloon by the casting process was found sufficient to maintain the balloon in an at least partially inflated state for extended periods. The tests showed rather complete loss of $SF_6$, however, possibly due to pores or microcracks in the membrane, or inadequate sealing of the sock-like membranes when they were closed to form the tab 11, so it appeared that the test balloons did not rely on residual $SF_6$ to hold their inflation or shape. The presence of water vapor in some balloons after the test also indicated that either the solvent casting technique or the sealing techniques employed to close the balloon should be carefully controlled. Overall, however, applicant's experience to date indicates that synthetic bubbles having an appropriately compliant skin approximately three to twelve mils thick may be readily fabricated and will maintain appropriate inflation characteristics when implanted to both displace fluid in the middle ear and allow a degree of compressibility that allows a range of normal compliance of the round window when sound is propagated through the inner ear.

The synthetic bubble as described is sized to allow its placement in the hypotypanic cavity of most patients, and is short enough to not interfere with the sound transmission structures in the upper part of the cavity.

When surgically inserting the balloon, it is preferably positioned within the hyptoympanum as close as possible to the round window, and may be anchored in position temporarily with a resorbable packing material such as gel foam, grafting material, or silastic sheeting, such that mucosal folds or adhesions form postoperatively to secure the bubble in position. Thus located, the bubble hydraulically decouples the walls of the middle ear, and to the extent it displaces liquid, also decreases the mass of material that must be displaced by flexing of the round window.

The synthetic bubble and surgical method of the invention have been described with reference to one specific shape of synthetic bubble and several presently preferred materials for membrane construction and gas fill. It will be understood, however, that practical embodiments of the invention may take diverse shapes and be implemented with a variety of materials, to achieve a compressible gas bubble in a fluid-filled middle ear to allow normal displacement of the round window. Having disclosed a preferred embodiment and discussed operative technical considerations, various modifications, substitutions and improvements will occur to those skilled in the art, and these are considered to fall within the scope of the invention to which an exclusive right is claimed.

What is claimed is:

1. A method of treating hearing loss due to middle ear fluid congestion, such method comprising the step of implanting in a patient's middle ear within a defined hypotympanic cavity between the eardrum and the round window of a patient's ear a pliant membrane of biocompatible material formed into a gas-filled closed synthetic bubble substantially impermeable to body fluids such that the bubble remains inflated to displace fluid from about the round window allowing compliant motion thereof and such that said closed bubble contains a reservoir of at least one gas at a pressure effective to transmit pressure changes and sound vibrations acoustically through said closed bubble.

2. A method of treating hearing loss due to middle ear fluid congestion, such method comprising the step of implanting between an eardrum and a round window of a patient's ear a pliant membrane of biocompatible material formed into a gas-filled synthetic bubble for prolonged contact with body fluids while being substantially impermeable to such fluids such that the bubble remains inflated to displace fluid from about the round window allowing compliant motion thereof, and providing an initial mixture of gases inflating the bubble at partial pressure to cause osmotic self-inflation after implantation.

3. The method of claim 2, wherein the step of implanting the bubble includes implanting the bubble in a patient's ear proximate to the round window of the ear and anchoring the synthetic bubble in position with an anchor formed of resorbable packing.

* * * * *